US005540848A

United States Patent [19]

Engelhard

[11] Patent Number: 5,540,848

[45] Date of Patent: Jul. 30, 1996

[54] FILTER RETAINER FOR WATER PURIFICATION UNIT

[75] Inventor: Rolf Engelhard, Prescott, Ariz.

[73] Assignee: Vortex Corporation, Scottsdale, Ariz.

[21] Appl. No.: 355,069

[22] Filed: Dec. 13, 1994

[51] Int. Cl.[6] .......... C02F 1/32; C02F 1/78

[52] U.S. Cl. .......... 210/748; 210/192; 210/205; 210/450; 210/451; 210/453; 210/760; 210/764; 250/436; 422/24; 422/186.3

[58] Field of Search .......... 210/748, 192, 210/760, 764, 198.1, 205, 450, 451, 453; 422/24, 186.3; 250/435, 436, 437, 438; 261/DIG. 42

[56] References Cited

U.S. PATENT DOCUMENTS

| | | | |
|---|---|---|---|
| 2,713,946 | 7/1955 | Abrams | 210/164 |
| 3,528,554 | 9/1970 | Ogden et al. | 210/343 |
| 4,352,735 | 10/1982 | Turetsky | 210/238 |
| 4,497,706 | 2/1985 | Pickett et al. | 210/130 |
| 4,680,116 | 7/1987 | Kamiwada et al. | 210/282 |
| 5,266,215 | 11/1993 | Engelhard | 210/748 |

OTHER PUBLICATIONS

"Wave Spring Washers", catalog sheet of Associated Spring Raymond Barnes Group, Inc., p. 18, date unknown.

"Finger Spring Washers", catalog sheet of Associated Spring Raymond Barnes Group, Inc., p. 16, date unknown.

*Primary Examiner*—Neil McCarthy

*Attorney, Agent, or Firm*—Cahill, Sutton & Thomas P.L.C.

[57] ABSTRACT

Water to be purified swirls about a source of ultraviolet radiation to kill any microorganisms contained therein and flows through a carbon filter cartridge mounted about the ultraviolet source to remove any chlorine and particulate matter. The outflow from the carbon filter is again subjected to ultraviolet radiation to kill any microorganisms entrained in the water emanating from the carbon filter. An ozone generator may be incorporated to entrain ozone with the inflowing water to enhance killing of any microorganisms present and to oxidize any undesirable compounds. The cartridge filter has its annular support member at one end disposed adjacent a first annular ridge to establish an annular seal between the support member and the first annular ridge. An axially moveable disk includes a second annular ridge disposed adjacent the annular support member at the other end of the cartridge filter to establish an annular seal therebetween. A spring washer urges the disk toward the cartridge filter and urges the cartridge filter toward the first annular ridge to maintain the respective annular seals despite aging or degradation of the annular support members of the cartridge filter.

21 Claims, 3 Drawing Sheets

PURIFIED WATER OUT

FILTER RETAINER FOR WATER PURIFICATION UNIT

CROSS-REFERENCE TO RELATED PATENT

The present application describes apparatus related to an invention by the present inventor and disclosed in U.S. Pat. No. 5,266,215, issued Nov. 20, 1993.

BACKGROUND OF THE INVENTION

1. Field of the Invention

The present invention relates to water purification systems and, more particularly, to apparatus for sealingly retaining a cartridge filter in place in a water purification unit.

2. Description of Related Art

For decades various water filtering and purifying devices have been used by consumers. Some of these devices perform primarily only a particulate filtering function to remove particulate matter. Some of these systems incorporate activated charcoal as a filtering medium to remove chlorine from the water obtained from municipal water sources. Some devices incorporate a source of ultraviolet light to help kill living microorganisms. To enhance such killing and to oxidize various compounds in the water, ozone may be injected into and mixed with the water.

While activated charcoal cartridge filters can be very effective in removing particulate matter and chlorine from water, they suffer major drawbacks. The contaminants or sludge filtered from the water will collect upon the filter. The sludge, particularly when it contains organic matter, serves as a breeding ground for bacteria, viruses and other microorganisms. These microorganisms often are conveyed downstream from the filter and are ultimately ingested by the consumer. Due to aging the normally compressible annular cartridge filter seating elements or annular support members may lose their sealing capability and permit bypass of water to be filtered. These potential health hazards can be avoided to some extent by regular replacement of the cartridge filter. Unfortunately, such replacement is often neglected by a consumer and the resulting health hazards may be life threatening. To avoid and eliminate such health hazards, the use of consumer oriented water filtering devices having mechanical filters for removing particulate matter has been banned in various communities around the world.

SUMMARY OF THE INVENTION

Water to be purified flows within a canister in a swirling pattern about a source of ultraviolet radiation to subject any living microorganisms to the killing effect of ultraviolet radiation. The water flows through a cartridge filter to remove particulate matter and also chlorine if the filter contains activated charcoal. Outflow from the filter is again subjected to ultraviolet radiation to kill any microorganisms that grew in residue upon the filter and subsequently became entrained in the outflowing water. To enhance killing of any microorganisms, an ozone generator may be incorporated to provide ozone for entrainment with water inflowing to the canister. To ensure that filtration is not compromised by loss of sealing capability at opposed ends of the cartridge filter, sealing elements are biased to compress annular support members at opposed ends of the cartridge filter by a spring washer.

It is therefore a primary object of the present invention to provide a water purification apparatus having an outflow free of living microorganisms and particulate matter.

Another object of the present invention is to provide a water purification apparatus with a support for sealing the ends of a cartridge filter encircling a source of ultraviolet radiation for killing microorganisms flowing into and out of the cartridge filter.

Still another object of the present invention is to provide apparatus for spring loading the seals at opposed ends of a cartridge filter within a canister of a water purification apparatus.

Yet another object of the present invention is to provide a water purification apparatus having a readily replaceable cartridge filter retained in place by spring loaded seals to prevent bypass of water to be filtered.

A further object of the present invention is to provide a spring washer for urging sealing at opposed ends of a cartridge filter mounted within a water purification apparatus to maintain effective sealing despite aging of the compressible material at opposed ends of the cartridge filter.

A yet further object of the present invention is to provide a spring washer for urging a support disk adjacent an end of a cartridge filter disposed in a water purification apparatus to maintain the seal between the disk and the adjacent end of the cartridge filter.

A yet further object of the present invention is to provide a fixed annular ridge adjacent one end of a cartridge filter and a moveable disk having an annular ridge disposed adjacent the other end of the cartridge filter and a spring for urging the moveable disk toward the cartridge filter to maintain both annular ridges in sealing engagement with the cartridge filter, which cartridge filter is mounted within a water purification apparatus.

A still further object of the present invention is to provide a method for maintaining seals at opposed ends of a cartridge filter mounted within a water purification apparatus to prevent filter bypass of the water to be purified.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which.

DESCRIPTION OF THE PREFERRED EMBODIMENT

Figures 1, 2A, 2B, 3A, 3B:
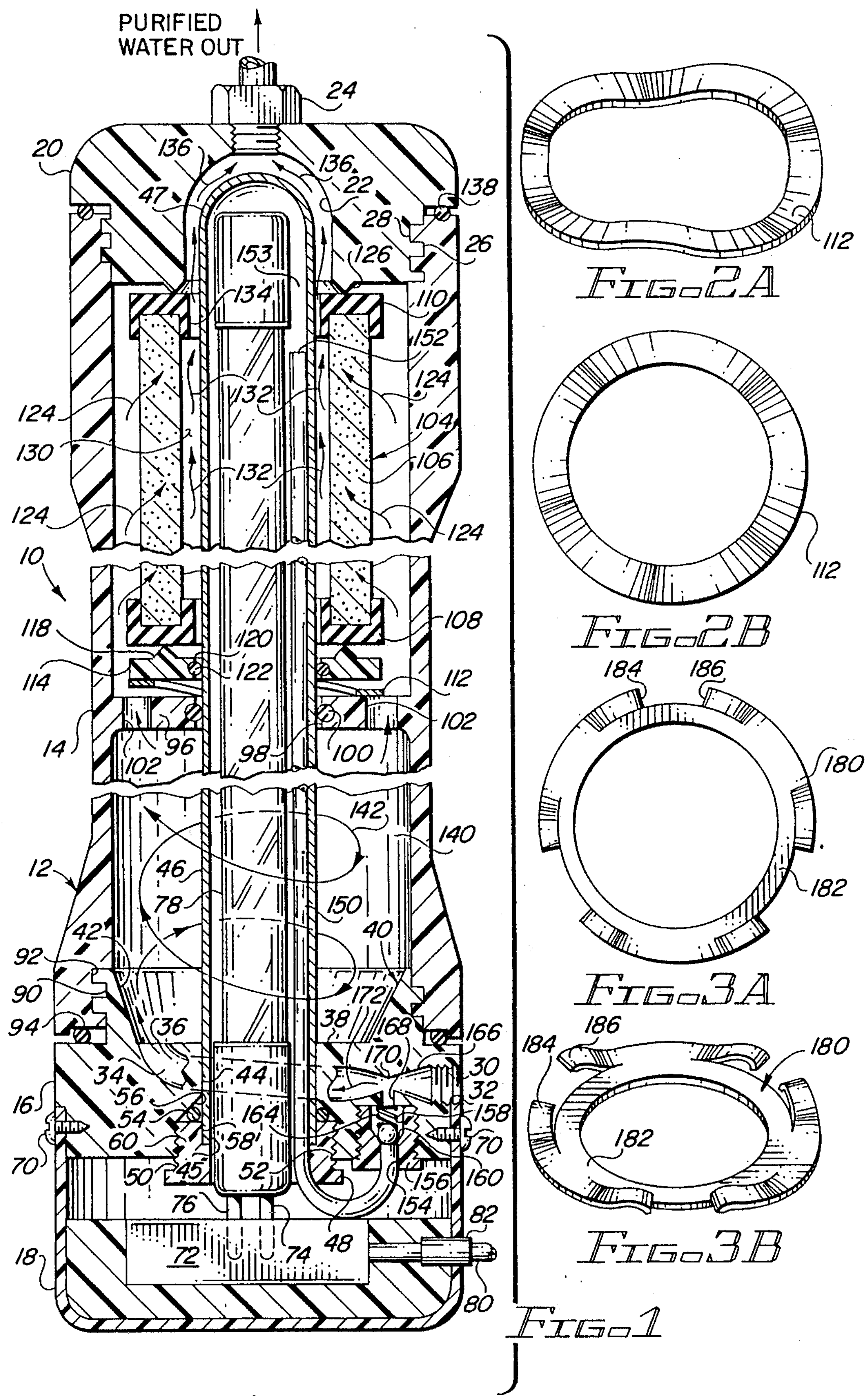
FIG. 1 is a cross-sectional view illustrating a water purification apparatus embodying the present invention.
FIG. 2A illustrates a three-quarter view of a wave spring washer.
FIG. 2B is a plane view of the wave spring washer shown in FIG. 2A.
FIG. 3A is a plan view of a finger spring washer.
FIG. 3B is a three-quarter view of the finger spring washer shown in FIG. 3A.

Referring to FIG. 1, there is illustrated a water purification apparatus 10 in the general shape of a canister 12. The canister includes a central sleeve member 14 for conveying water longitudinally therein during purification. The canister is detachably attached to a water inlet member 16. A base 18 attached to the water inlet member supports canister 12. A top member 20 is detachably attached to the upper end of sleeve member 14 for closing the upper end of the sleeve member and for providing an outlet for the water purified within water purification apparatus 10.

As shown in FIG. 1, water inlet member 16 includes an inlet 30, which inlet may include internal threads 32 for threaded engagement with a nipple or conduit conveying water to the water inlet member. The inlet is in communication with a passageway 34 for conveying the inflowing water to outlet 36, which outlet is disposed in base 38 of depression 40 formed in water inlet member 16. The orientation of outlet 36, in combination with the adjacent section of passageway 34, directs the outflow against cone shaped wall 42 of depression 40 to induce a circular or swirling motion of the inflowing water. A passageway 44 extends through the center of water inlet member 16 for receiving and supporting the bottom open end 45 of a tube 46 having a closed top end 47. An apertured collar 48 is in threaded engagement with threads 50 disposed in radially expanded section 52 of passageway 44. An O-ring 54 encircles bottom end 45 of tube 46 adjacent shoulder 56 of passageway 44. Collar 48 may include a radially expanded depression 58 for receiving and supporting bottom end 45 of tube 46. Upon tightening of collar 48, tube 46 is moved axially within passageway 44 due to the force exerted upon it by the lower end (shoulder) of depression 58. O-ring 54 will be compressed between shoulder 56 and the adjacent cylindrical surface of tube 46 by end 60 of the collar to form a water tight seal between the cylindrical surface of the tube and passageway 44.

Base 18, being cup shaped, as illustrated, may be secured to water inlet member 16 by fastening means, such as screws 70. A socket 72 is formed within the base to support and electrically engage prongs 74, 76 of ultraviolet (UV) light 78. This light emits ultraviolet radiation; necessarily, tube 46 must be transmissive to such radiation and it is therefore preferable that the tube be made of quartz or similar material. Socket 72 also includes an electrical circuit necessary to energize ultraviolet (UV) light 78. Electrical power for the circuit is provided by conductor 80 extending from base 18 through grommet 82 or the like. Conductor 80 is electrically connected to a source of electrical power (not shown) such as a source of 12 vdc.

Sleeve member 14 includes internal threads 90 for threadedly engaging threads 92 at the upper end of water inlet member 16 and encircling depression 40. Upon threaded engagement between the sleeve member and the water inlet member, O-ring 94 disposed therebetween is compressed to provide a watertight engagement. A radial flange 96 disposed within sleeve member 14 includes a central aperture 98 for accommodating penetrable engagement of tube 46.

An o-ring 100 disposed therebetween prevents water flow intermediate tube 46 and aperture 98 of flange 96. A plurality of passageways 102 are disposed in flange 96 to permit water flow therethrough into the upper end of sleeve member 14.

A filter cartridge 104, which may be of any one of many types of commercially available filter cartridges, is penetrably mounted upon tube 46; it may include activated carbon/charcoal to remove chlorine and other similar compounds. Such a cartridge includes a cylindrical filter element 106 having annular support members 108,110 disposed at opposed ends. These support members are generally of rubber, neoprene, or the like. A spring washer, such as wave spring washer 112, rests upon flange 96 and receives support therefrom. A filter support disk 114 rests upon the wave spring washer. This disk includes an annular ridge 116 which, in compressive engagement with annular support member 108, establishes a seal therebetween. Such seal precludes water flowing through passageways 102 of flange 96 from flowing to the interior of the filter cartridge intermediate the filter support disk and annular support member 108. Furthermore, an O-ring 120 is disposed intermediate central aperture 122 of the filter support disk and tube 46. Typically, the spring rate of wave spring washer 112 is linear between twenty percent (20%) to eighty percent (80%) of available deflection and thereby provides essentially constant pressure against cartridge filter 104 to maintain the seal between annular ridge 118 and annular support member 108. Accordingly, all water flowing from passageways 102 flows to the exterior of filter element 106, as depicted by arrows 124, and through the filter element. Top member 20 includes a similar annular ridge 126 for compressively engaging annular support member 110 to prevent water flowing to the interior of the filter cartridge between the top member and the upper end of filter cartridge 104. Thus, all water flowing through passageways 102 must flow through the filter cartridge from the outer surface to the inner surface of the filter element.

Support members 108 and 110 are annular in configuration and may have internal diameters greater than the diameter of tube 46, as depicted. Water flowing through filter element 106, as depicted by arrows 124, flows into the annular space interior of the filter element and adjacent tube 46, which space is identified by numeral 130. The water flow through space 130 is upwardly, as depicted by arrows 132. Outflow from space 130 is through the annular channel defined between inner annular surface 134 of support member 110 and the cylindrical surface of tube 46.

Top member 20 includes a depression 22 for receiving top end 47 of tube 46. The depression is sized sufficiently greater than the top end of the tube to permit flow of water adjacent the tube, as depicted by arrows 136. An outlet fixture 24 is secured to and extends from top member 20 to accommodate outflow of water from depression 22. Top member 20 is detachably attached to the upper end of sleeve member 14 by threads 26 of the top member engaging threads 28 of the sleeve member. A water tight fit is assured by O-ring 138 compressed between the top member and the sleeve member upon threaded engagement therebetween.

In operation, water to be filtered enters through inlet 30 in water inlet member 16 and is discharged through outlet 36. The angle of discharge causes the water to flow in a circular path within compartment 140 in sleeve member 14 in a helical manner, as depicted by helical arrow 142. The circular water flow is enhanced in part by cone shaped wall 42 in the water inlet member. The water swirling about tube 46 in compartment 140 is subjected to UV radiation from UV light 78. As is well known, any living microorganisms, whether bacteria, viruses, etc. will be killed upon UV irradiation. Moreover, certain compounds, if present in the water, may be oxidized to enhance purification of the water. The water swirling about tube 46 will enhance exposure of all of the living microorganisms to UV radiation and thereby a more complete killing of the microorganisms is enhanced. The swirling water will also perform a scrubbing action upon tube 46 to help maintain it clean and clear. The swirling water ultimately flows through passageways 102 to the outer surface of filter element 106. Flow of the water through the filter element will cause removal of particulate matter, including dead living microorganisms. The water discharged from the interior surface of filter element 106 flows adjacent tube 46, as depicted by arrows 132 to again subject the water to UV irradiation. Any living microorganisms entrained in the water flowing from the filter element will be killed through the resulting UV irradiation. Furthermore, the inner surface of the filter element from which the water is discharged will be irradiated by UV to kill any residual microorganisms that may attempt to grow there. The filtered and purified water flows into depression 22 and is discharged through outlet 24 to a point of use.

At greater or lesser intervals, depending upon the degree of contamination of the inflowing water, filter cartridge 104 should be replaced. Such replacement is readily effected by simply unscrewing top member 20 from sleeve member 14 and withdrawing the cartridge filter from about tube 46. A replacement filter is mounted upon the tube and the top member is screwed on to the sleeve member to lock the filter in place and provide a watertight seal between the sleeve member and the top member.

The water purification unit described above purifies water by subjecting the water to ultraviolet radiation and by filtering entrained matter. As depicted in FIG. 1, the water purification unit also provides a further capability of generating ozone and entraining the generated ozone in the inflowing water to enhance killing of any microorganisms and to enhance oxidation of certain compounds. It is well known that ultraviolet radiation in air will alter the molecular structure of oxygen ($O_2$) to produce ozone ($O_3$). Since ultraviolet light 78 is located in an air environment or air space within tube 46, some of the oxygen molecules in the air space between the light and the tube will be converted to ozone molecules. Furthermore, these ozone molecules will collect at closed top end 47 of tube 46. A conduit 150 is disposed within tube 46 adjacent UV light 78 (see also FIG. 4). Inlet 152 of the conduit is disposed in an air space 153 proximate the top end 47 of tube 46. The lower end of the conduit extends from within tube 46 into passageway 154 of a plug 156. The plug is in threaded engagement with water inlet member 16. A radially expanded section 158 of passageway 154 includes cone shaped annular bottom surface 160. A ball 162, located adjacent surface 160 in response to a coil spring 164, serves in the manner of a check valve to permit flow from conduit 150 into expanded section 158 but not in reverse. Inlet 30 for the water to be purified, is directed through a venturi section 166. A passageway 168 interconnects expanded section 158 with the diametrically restricted section 170 of venturi section 166. As is well known, and in accordance with the Bernoulli principle, the pressure at section 170 will be below ambient pressure. Accordingly, an inflow of ozone, as depicted by arrow 172 will occur. The inflow results in a reduced pressure in expanded section 158 below that present within conduit 150. Because of the difference in pressure on opposed sides of ball 162, the check valve will open. Accordingly, ozone will be drawn from conduit 150 into expanded section 158, through conduit 168 and into section 170. Reverse flow through the check valve is precluded by the sealing engagement of ball 162 with the outlet of conduit 150 under urging of coil spring 164. It may be noted that an O-ring or other sealing member may be incorporated intermediate plug 156 and water inlet member 16 to ensure that water will not leak into base 18.

The water flow from inlet 30 through venturi section 166 will draw a flow of air, and any ozone present, into inlet 152 of conduit 150 for discharge past ball 162 through expanded section 158 and into section 170. The resulting entrainment of air and ozone will be swirled about tube 46 in compartment 140, as depicted by arrow 142. The presence of ozone in the water, will, by itself, result in killing of living microorganisms present and oxidation of certain compounds, if present. Thus, any living microorganisms present in the water within sleeve member 14 will be subjected to the killing effect of both UV radiation from light 78 and ozone. Filter element 106 of filter cartridge 104 will remove any particulate matter that may be present, including residue of any killed microorganisms. To the extent ozone flows into filter element 106, it will kill any living microorganisms on the surface of the filter into which the water flows. To the extent that any living organisms are entrained in the water outflowing from the interior surface of filter element 106, they are again irradiated with UV radiation from light 78 prior to discharge through outlet 24. To the extent any ozone may be present in the water flowing through and from the filter element, killing of the microorganisms will be enhanced.

Figure 4:
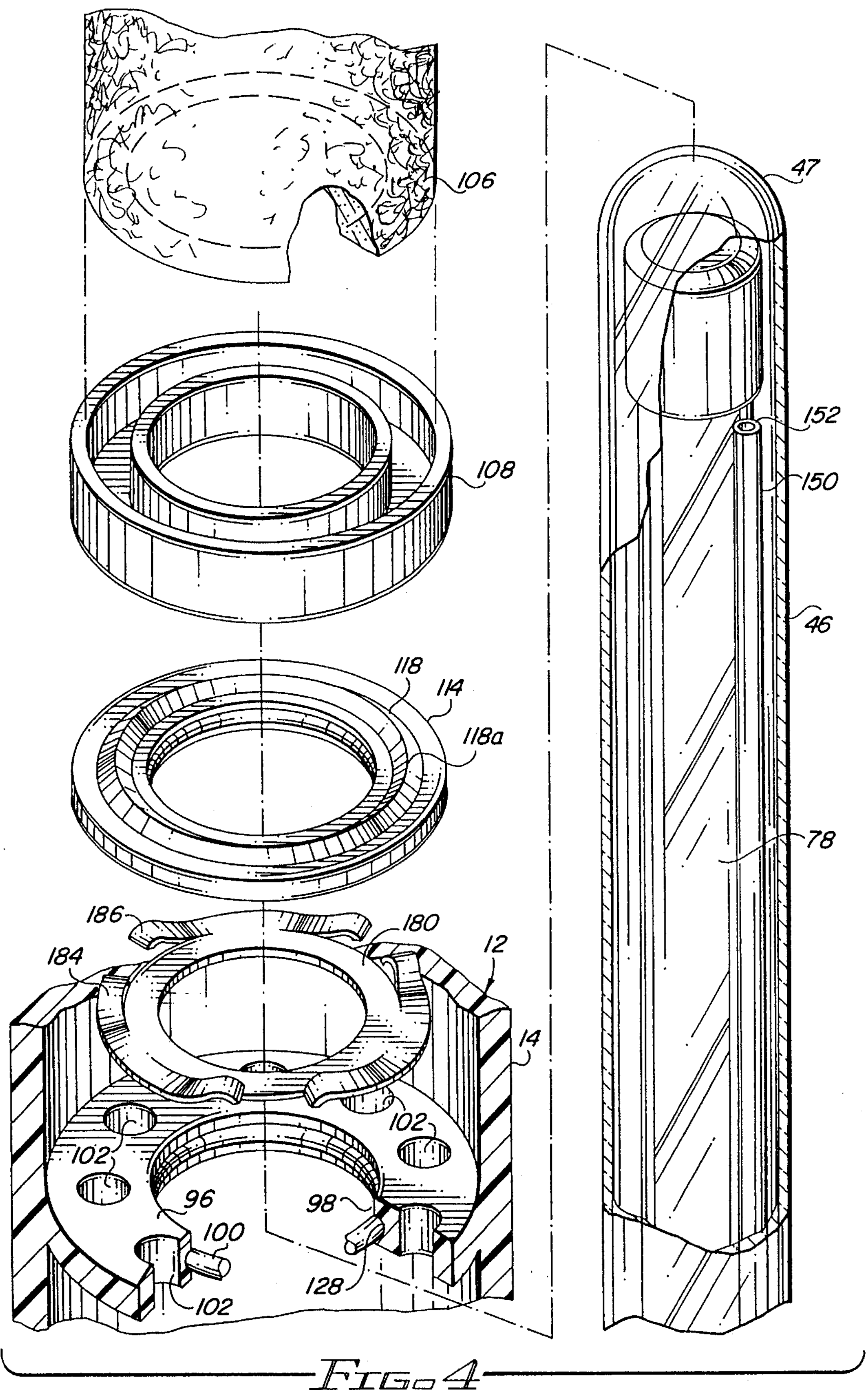
FIG. 4 is an isometric view illustrating the components attendant the spring support for a cartridge filter mounted within a water purification unit.

Referring to FIGS. 2A and 2B, there is shown a spring washer of the type referred to as a wave spring washer 112 useable in water purification unit 10, as described above, for the purpose of maintaining a seal at the annular ends of filter cartridge 104. The wave spring washer is annular in plan form, as illustrated in FIG. 2B, and includes a generally undulating surface, as shown in FIG. 2A, to provide the requisite spring action upon an attempt to flatten the wave spring washer. The resulting spring force bears upon filter support disk 114, as shown in FIGS. 1 and 4, to maintain annular ridge 118 in sealing engagement with annular support member 108, which member is generally of rubber or of similar flexible, resilient composition. The spring force exerted by wave spring washer 112 urges cartridge filter 104 upwardly. The upwardly urged movement creates an ongoing force between annular support member 110 (which is similar to annular support member 108) and downwardly oriented annular ridge 126 extending from top member 20 to maintain a seal therebetween. Such ongoing spring force to maintain the two seals is necessary in the event cartridge filter 104 is not replaced often enough to prevent hardening or loss of resiliency and flexibility of the respective annular support members. That is, these annular support members may take a set as a result of the annular indentation urged by the respective annular ridge and leakage may result. With the application of a spring force exerted by a spring washer, even if such set arises, the seals will tend to be maintained.

As particularly shown in FIGS. 3A and 3B, a spring washer of the type referred to as a finger spring washer 180 may be employed in place of wave spring washer 112. The finger spring washer includes an annular generally flat base 182. A plurality of opposed pairs of fingers 184,186 extend from the base and are canted or bent out of the plane of base 182 to provide a spring action upon urging of these fingers into the plane of base 182. As noted in FIG. 3B, the ends of each of these fingers may be bent toward base 182 to prevent gouging of an adjacent element upon compression of the finger spring washer. Finger spring washer 180 and wave spring washer 112 of the type discussed above are manufactured by Associated Spring Raymond Barnes Group, Inc. and by others.

Further details of the apparatus for preloading cartridge filter 104 to maintain seals at the opposed ends will be described with reference to FIG. 4. Radial flange 96 extends inwardly from central sleeve member 14 to support within aperture 98 tube 46 containing UV light 78 and possibly conduit 150 (if ozone is to be generated). O-ring 100 is disposed within a groove 128 in aperture 98 to establish a sealed engagement with tube 46 and prevent water flow intermediate the radial flange and the tube. Thus, all of the water flow flows through passageways 102 in the radial flange. A spring washer, such as finger spring washer 180, rests upon radial flange 96. The size of this spring washer must be commensurate with the size and location of passageways 102 to prevent significant impediment to water flow through the passageways. Fingers 184,186 of the finger spring washer urge filter support disk 114 upwardly toward annular support member 108 secured to the lower end of filter element 106. Such urged movement causes annular ridge 118 to bear against the annular surface of the annular support member and form a seal therebetween. Despite aging of the annular support member, the ongoing force exerted by the annular ridge thereagainst will maintain a seal for all practical purposes. The effectiveness of the seal may be enhanced by forming annular ridge 118 with a knife edge 118A.

Figure 5:
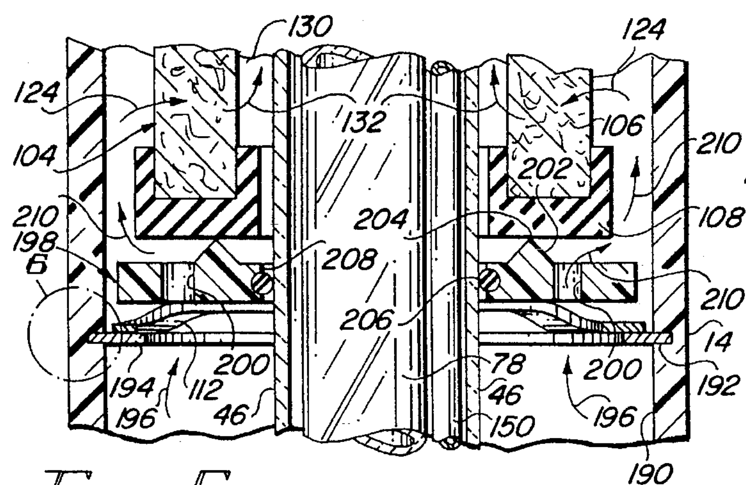
FIG. 5 is a detail sectional view of a variant mounting for a wave spring washer and associated sealing disk.
Figure 6:
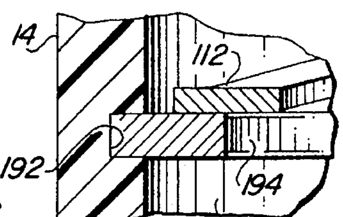
FIG. 6 is a detail view taken within circle 6 shown in FIG. 5.

Referring jointly to FIGS. 5 and 6, a variant assembly for supporting the lower end of cartridge filter 104 will be described. Interior wall 190 of central sleeve member 14 may include a groove 192 for partially receiving and supporting a snap ring 194. As the snap ring is centrally apertured, water will flow therethrough, as depicted by arrows 196. A spring washer, such as wave spring washer 112, rests upon the exposed annular surface of snap ring 194. A variant filter support disk 198 is supported upon the spring washer. It includes a plurality of passageways 200 to accommodate water flow therethrough. Since the perimeter of the variant disk may not extend all the way to interior surface 190 of the central sleeve member, an amount of water flow may bypass the disk. Each of passageways 200 is radially outwardly of an annular ridge 202 supporting filter cartridge 104. The ridge may include a sharp edge or knife edge 204 to bear against the lower surface of annular support member 108 to establish an annular seal therewith. This annular seal precludes water outflowing from passageways 200 from flowing between annular support member 108 and variant disk 198 toward tube 46. An O-ring 206 disposed within aperture 208 of the variant disk seals variant disk 198 with tube 46 to preclude water flow therebetween. Accordingly, water outflowing from passageways 200 will flow radially outwardly and upwardly about the lower end of cartridge filter 104, as depicted by arrows 210.

Figure 8:
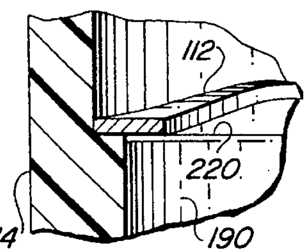
FIG. 8 is a detail view taken within circle 8 shown in FIG. 7.
Figure 7:
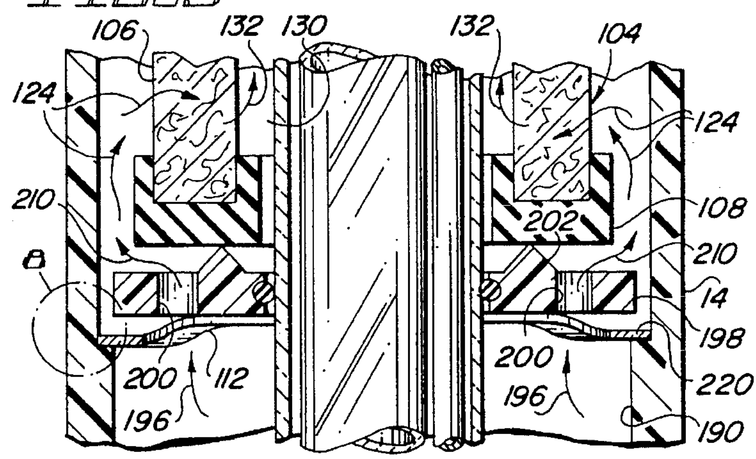
FIG. 7 is a detail sectional view of a further variant mounting for a finger spring washer and an associated sealing disk.

Referring jointly to FIGS. 7 and 8, a variant of the support for the spring washer will be described. To avoid the parts and labor costs associated with insertion and retention of a snap ring, as shown in FIG. 5, a shoulder 220 is formed in interior surface 190 of central sleeve member 14. This shoulder supports a spring washer, such as wave spring washer 112. As described above with respect to FIG. 5, variant filter support disk 198 rests upon wave spring washer 112. As a result of the spring force exerted by the wave spring washer, annular ridge 202 of the variant filter support disk bears against and forms a seal with annular support member 108 of filter cartridge 104. As depicted by arrows 196, the water beneath the wave spring washer and within central sleeve member 14 flows upwardly through the central aperture of the wave spring washer into passageways 200 of the variant disk and intermediate the perimeter of the variant disk and interior surface 190. Therefrom, as depicted by arrows 210 and 124, the water flows about the perimeter of annular support member 108 and through filter element 106. The filtered water flows upwardly within space 130 adjacent tube 46, as depicted by arrows 132.

It is understood that either wave spring washer 112 or finger spring washer 180 may be supported by either snap ring 194 and related structure or by shoulder 220 and related structure.

Figure 9:
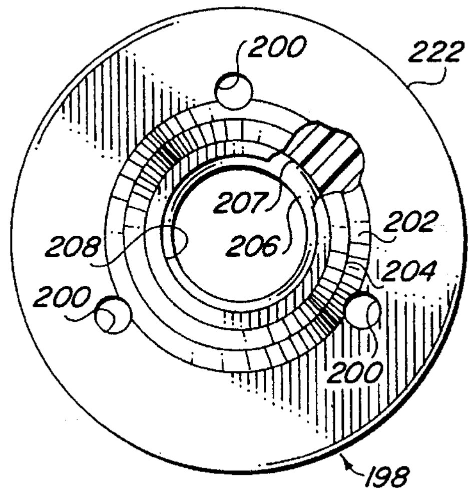
FIG. 9 is a plan view of the sealing disk.

FIG. 9 illustrates a plan view of variant filter support disk 198. The disk includes a plurality of passageways 200 extending therethrough for accommodating water flow irradiated by the UV light source. An annular ridge 202 extends upwardly from the plane of the variant disk. This annular ridge is generally radially inwardly of passageways 200. The upper extremity of the annular ridge may include a knife edge 204 to bear against a corresponding annular area of the adjacent annular support member of the filter cartridge. The knife edge represents a relatively small area and the force exerted by the supporting spring washer will create a relatively significant pressure to enhance formation and maintenance of a seal between the annular ridge of the variant disk and the corresponding annular area of the annular support member of the cartridge filter. An O-ring 206 is disposed in a groove 207 formed in the sidewall of aperture 208. This O-ring establishes a seal about tube 46 to prevent water flow intermediate the variant disk and the tube.

Figure 10:
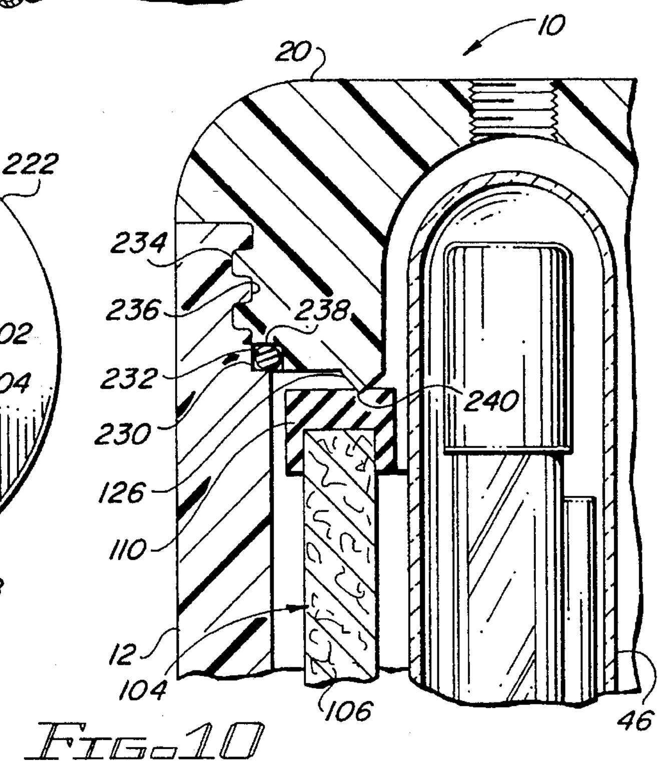
FIG. 10 illustrates a variant of the seal for the top member of the water purification unit.

FIG. 10 illustrates a variant sealing apparatus between top member 20 and canister 12 from that depicted in FIG. 1. A shoulder 230 is formed in the interior cylindrical part of the canister to support an O-ring 232. Threads 234 and 236 of the top member and the canister establish threaded engagement therebetween. An indentation 238 at the lower end of threads 234 receives O-ring 232. Upon threaded engagement between the top member and the canister, O-ring 232 will be compressed between shoulder 230 and indentation 238 to form a seal intermediate the top member and the canister to prevent water leakage through the associated threaded engagement.

As further noted in FIG. 10, annular support member 110 extends about the upper end of filter element 106 of cartridge filter 104. Annular ridge 126 extends downwardly from top member 20 and includes an edge 240 that may be a knife edge. Upon insertion of a cartridge filter within the canister and threaded engagement of top member 20 with the canister, annular ridge 126 will engage annular support member 110. Such engagement will result in a seal formed between annular ridge 126 and annular support member 110. Maintaining this seal is enhanced by the upward force urged by the spring washer disposed at the lower end of the cartridge filter, as illustrated in FIGS. 1, 5, and 7. Thus, any aging or degradation of the flexibility and resilience of the annular support member will tend to be overcome by the continuing urging of the annular support member against the sharp edge 240 of annular ridge 126.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

I claim:

1. In a water purification unit having a source of UV radiation for killing microorganisms present in the water to be purified, a cartridge filter for filtering the water to remove particulate matter from the water to be purified, a compartment for irradiating unfiltered water with UV radiation from the UV source, passageways for channeling the irradiated unfiltered water through the cartridge filter, and a space for irradiating the filtered water with UV radiation from the UV source, the improvement comprising in combination:

(a) a first annular ridge in sealing engagement with one end of the cartridge filter;

(b) a second annular ridge in sealing engagement with the other end of the cartridge filter;

(c) a disk for supporting said second annular ridge; and (d) a spring washer for urging said disk toward the cartridge filter and the cartridge filter toward said first annular ridge to maintain the sealing engagement between each end of the cartridge filter and the respective ones of said first and second annular ridges, said disk and spring washer encircling the source of UV radiation at a position separating the compartment for irradiating the unfiltered water and the space for irradiating the filtered water.

2. The improvement as set forth in claim 1 including a compartment for swirling the unfiltered water about said UV source to enhance exposure of any water entrained microorganisms to UV irradiation.

3. The improvement as set forth in claim 2 including mounting means for said UV source for penetrably engaging the cartridge filter with the UV source.

4. The improvement as set forth in claim 3 wherein the UV source comprises an elongated lamp and wherein the cartridge filter includes an outer cylindrical surface and an inner cylindrical surface and wherein said inner cylindrical surface is juxtaposed with said lamp to expose said inner cylindrical surface to irradiation from the UV source.

5. The improvement as set forth in claim 1 wherein the UV source comprises an elongated cylindrical lamp and including an UV transmissive tube for surrounding and for protecting the lamp.

6. The improvement as set forth in claim 5 wherein the cartridge filter includes outer and inner cylindrical surfaces and wherein said disk penetrably supports said cartridge filter about said tube.

7. The improvement as set forth in claim 6 wherein said disk channels unfiltered irradiated water to the outer cylindrical surface of the cartridge filter.

8. The improvement as set forth in claim 1 including an ozone generator for generating ozone within said unit and an entrainer for entraining the ozone with the water to be purified to kill microorganisms.

9. The improvement as set forth in claim 8 including an inlet for introducing to said unit water to be filtered and wherein said entrainer comprises a venturi for entraining the ozone with the water introduced through said inlet.

10. The improvement as set forth in claim 9 wherein said ozone generator comprises an air space adjacent said UV source and interior of said tube and wherein said entrainer includes a conduit extending from the air space to said venturi.

11. Apparatus for mounting and sealing the opposed ends of a cartridge filter within a water purification unit which purifies the water by killing microorganisms in both filtered and unfiltered water with radiation from an internally mounted UV lamp and filters entrained matter from UV irradiated water with the cartridge filter, said apparatus comprising in combination:

(a) a first annular ridge disposed proximate one end of the cartridge filter for sealingly engaging a first annular support member at the one end of the cartridge filter;

(b) a moveable disk having a second annular ridge for sealingly engaging a second annular support member at the other end of the cartridge filter; and (c) a spring washer for urging movement of said disk toward the cartridge filter and for urging movement of the cartridge filter toward said first annular ridge to maintain each of the first and second annular members in sealing engagement with the respective ones of said first and second annular ridges, wherein said moveable disk and said spring washer encircle the internally mounted uv lamp at a position separating a compartment for irradiating the unfiltered water and a space for irradiating the filtered water.

12. The apparatus as set forth in claim 11 including a support member for supporting said spring washer.

13. The apparatus as set forth in claim 11 wherein said disk includes passageways for accommodating water flow therethrough.

14. The apparatus as set forth in claim 11 wherein each of said first and second annular ridges includes a knife edge.

15. The apparatus as set forth in claim 11 wherein said spring washer comprises a wave spring washer.

16. The apparatus as set forth in claim 11 wherein said spring washer comprises a finger spring washer.

17. The apparatus as set forth in claim 12 wherein said support member comprises an annular shoulder.

18. The apparatus as set forth in claim 12 wherein said support member comprises a snap ring.

19. A method for mounting and sealing the opposed ends of a cartridge filter within a water purification unit which purifies water by killing microorganisms in both filtered and unfiltered water with radiation from an internally mounted UV lamp and filters entrained matter from UV irradiated water with the cartridge filter, said method comprising the steps of:

(a) sealingly engaging a first annular support member at one end of the cartridge filter with a first annular ridge disposed proximate the one end of the cartridge filter;

(b) sealingly engaging a second annular support member at the other end of the cartridge filter with a moveable disk having a second annular ridge; and (c) urging movement of the disk toward the cartridge filter and movement of the cartridge filter toward the first annular ridge with a spring washer to maintain each of the first and second annular members in sealing engagement with the respective ones of the first and second annular ridges, wherein the moveable disk and the spring washer encircle the internally mounted uv lamp at a position separating a compartment for irradiating the unfiltered water and a space for irradiating the filtered water.

20. The method as set forth in claim 19 including the step of supporting the spring washer.

21. The method as set forth in claim 20 including the step of accommodating flow of water through the disk.

* * * * *